US010368779B2

(12) United States Patent
Katsunuma

(10) Patent No.: US 10,368,779 B2
(45) Date of Patent: Aug. 6, 2019

(54) MAGNETIC RESONANCE IMAGING APPARATUS AND METHOD FOR CONTROLLING MAGNETIC RESONANCE IMAGING APPARATUS

(71) Applicant: TOSHIBA MEDICAL SYSTEMS CORPORATION, Otawara-Shi, Tochigi-Ken (JP)

(72) Inventor: Ayumi Katsunuma, Otawara (JP)

(73) Assignee: TOSHIBA MEDICAL SYSTEMS CORPORATION, Otawara-Shi, Tochigi-Ken (JP)

(*) Notice: Subject to any disclaimer, the term of this patent is extended or adjusted under 35 U.S.C. 154(b) by 674 days.

(21) Appl. No.: 14/337,587

(22) Filed: Jul. 22, 2014

(65) Prior Publication Data

US 2014/0336500 A1 Nov. 13, 2014

Related U.S. Application Data

(63) Continuation of application No. PCT/JP2013/081283, filed on Nov. 20, 2013.

(30) Foreign Application Priority Data

Nov. 22, 2012 (JP) ................................. 2012-256782

(51) Int. Cl.
*A61B 5/055* (2006.01)
*G01R 33/28* (2006.01)
(Continued)

(52) U.S. Cl.
CPC ............ *A61B 5/0555* (2013.01); *A61G 13/02* (2013.01); *G01R 33/28* (2013.01); *G01R 33/36* (2013.01);
(Continued)

(58) Field of Classification Search
CPC ...................................................... A61G 13/02
See application file for complete search history.

(56) References Cited

U.S. PATENT DOCUMENTS 3,913,153 A * 10/1975 Adams .................... A61G 7/018
318/65
5,611,638 A * 3/1997 Dorr .................... A61G 7/1019
403/321
(Continued)

FOREIGN PATENT DOCUMENTS

JP 63-216555 * 9/1988
JP 2004-329428 A 11/2004
(Continued)

OTHER PUBLICATIONS

International Search Report for PCT/JP2013/081283, dated Jan. 28, 2014.
(Continued)

*Primary Examiner* — Katherine L Fernandez
*Assistant Examiner* — Yi-Shan Yang
(74) *Attorney, Agent, or Firm* — Nixon & Vanderhye P.C.

(57) ABSTRACT

A magnetic resonance imaging apparatus of an embodiment includes: a bed top plate provided with a connector which can be coupled with a receiving coil; a bed which supports the bed top plate, the bed being configured to shift the bed top plate vertically and horizontally, the bed being configured to be jointly coupled with a stretcher apparatus having a stretcher top plate, and the stretcher top plate being placed on top of the bed top plate in a case where the stretcher apparatus is jointly coupled and; a bed controller configured to control a shift of the bed top plate correspondingly to at least one of a joint coupling condition between the bed and the stretcher apparatus and a coupling condition between the receiving coil and the connector.

17 Claims, 14 Drawing Sheets

(51) Int. Cl.
   *G01R 33/36* (2006.01)
   *A61G 13/02* (2006.01)
   *A61B 6/04* (2006.01)

(52) U.S. Cl.
   CPC ........ *A61B 6/0457* (2013.01); *A61G 2200/32* (2013.01); *A61G 2203/80* (2013.01)

(56) References Cited

U.S. PATENT DOCUMENTS

| | | | |
|---|---|---|---|
| 7,719,271 B2 | 5/2010 | Ohsawa | |
| 8,193,811 B2* | 6/2012 | Tropp | G01R 33/3415 324/318 |
| 2002/0174485 A1* | 11/2002 | Bartels | A61B 5/0555 5/601 |
| 2004/0102690 A1* | 5/2004 | Bartels | A61B 6/04 600/407 |
| 2005/0060047 A1* | 3/2005 | Schor | G01R 33/3635 700/19 |
| 2006/0058587 A1* | 3/2006 | Heimbrock | A61B 6/0457 600/300 |
| 2007/0039101 A1* | 2/2007 | Luginbuhl | A61B 5/0555 5/600 |
| 2007/0124858 A1* | 6/2007 | Ahlman | A61B 6/0442 5/81.1 R |
| 2008/0106262 A1* | 5/2008 | Ohsawa | G01R 33/34007 324/318 |
| 2008/0172789 A1* | 7/2008 | Elliot | A61G 7/0528 5/616 |
| 2009/0216110 A1* | 8/2009 | Piron | G01R 33/36 600/415 |
| 2010/0060284 A1 | 3/2010 | Sugiura | |
| 2010/0156420 A1* | 6/2010 | Driemel | A61B 5/0555 324/318 |
| 2010/0249575 A1* | 9/2010 | Shvartsberg | G01R 33/30 600/415 |
| 2012/0059242 A1* | 3/2012 | Caruba | A61B 5/0035 600/411 |
| 2013/0057283 A1 | 3/2013 | Takamori | |
| 2013/0184563 A1* | 7/2013 | Driemel | A61B 5/0555 600/415 |

FOREIGN PATENT DOCUMENTS

| | | |
|---|---|---|
| JP | 2009-082614 | 4/2009 |
| JP | 2009-165728 | 7/2009 |
| JP | 2011-143020 | 7/2011 |
| JP | 2012-213626 | 11/2012 |

OTHER PUBLICATIONS

English Translation of International Preliminary Report on Patentability dated May 26, 2015 for Application No. PCT/JP2013/081283.

JP Office Action dated Jul. 3, 2018 in JP 2013-239569.

\* cited by examiner

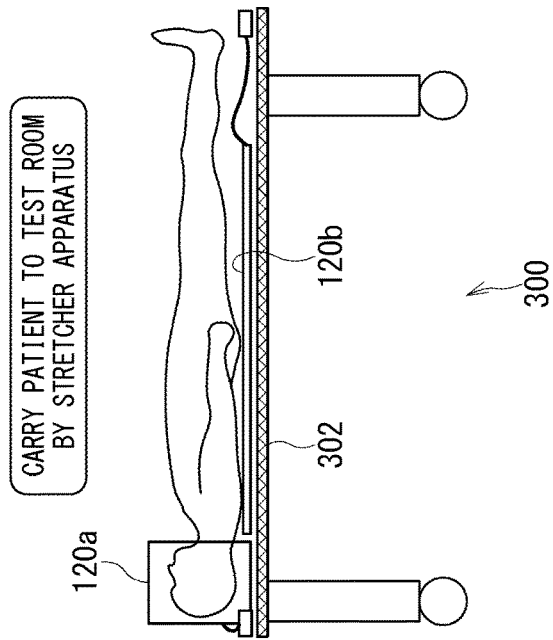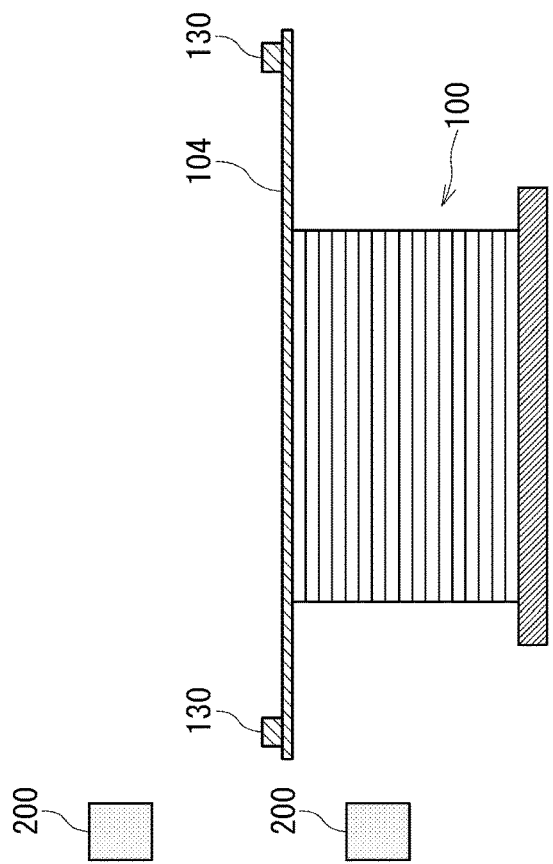
FIG. 7A
FIG. 7B

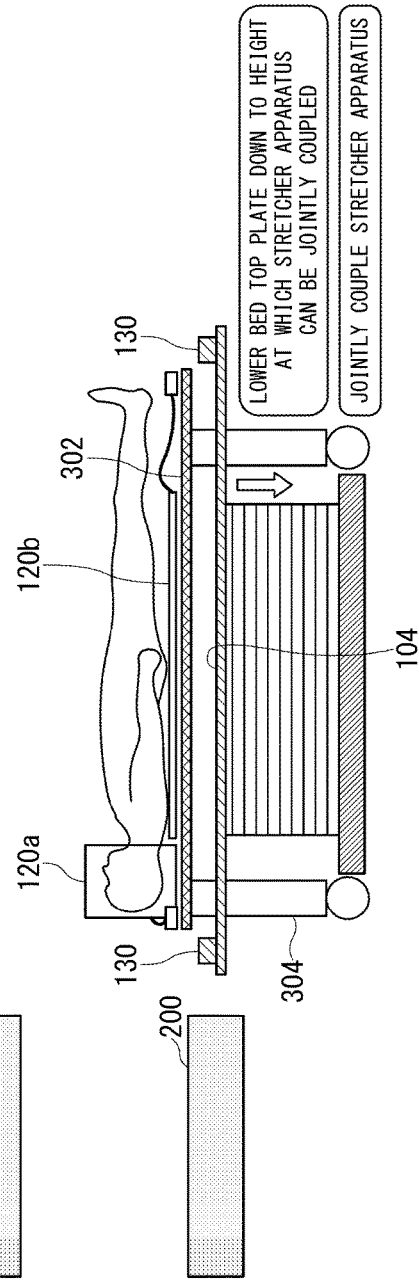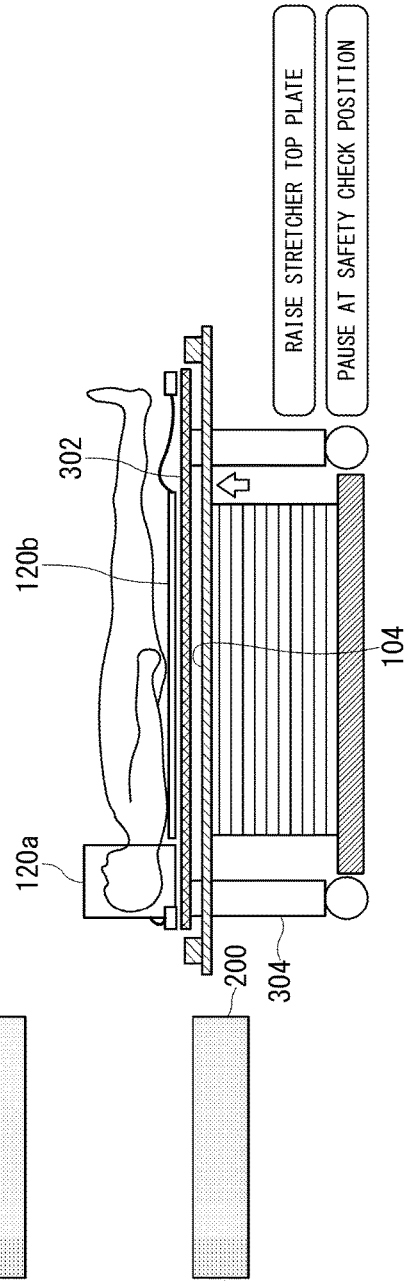

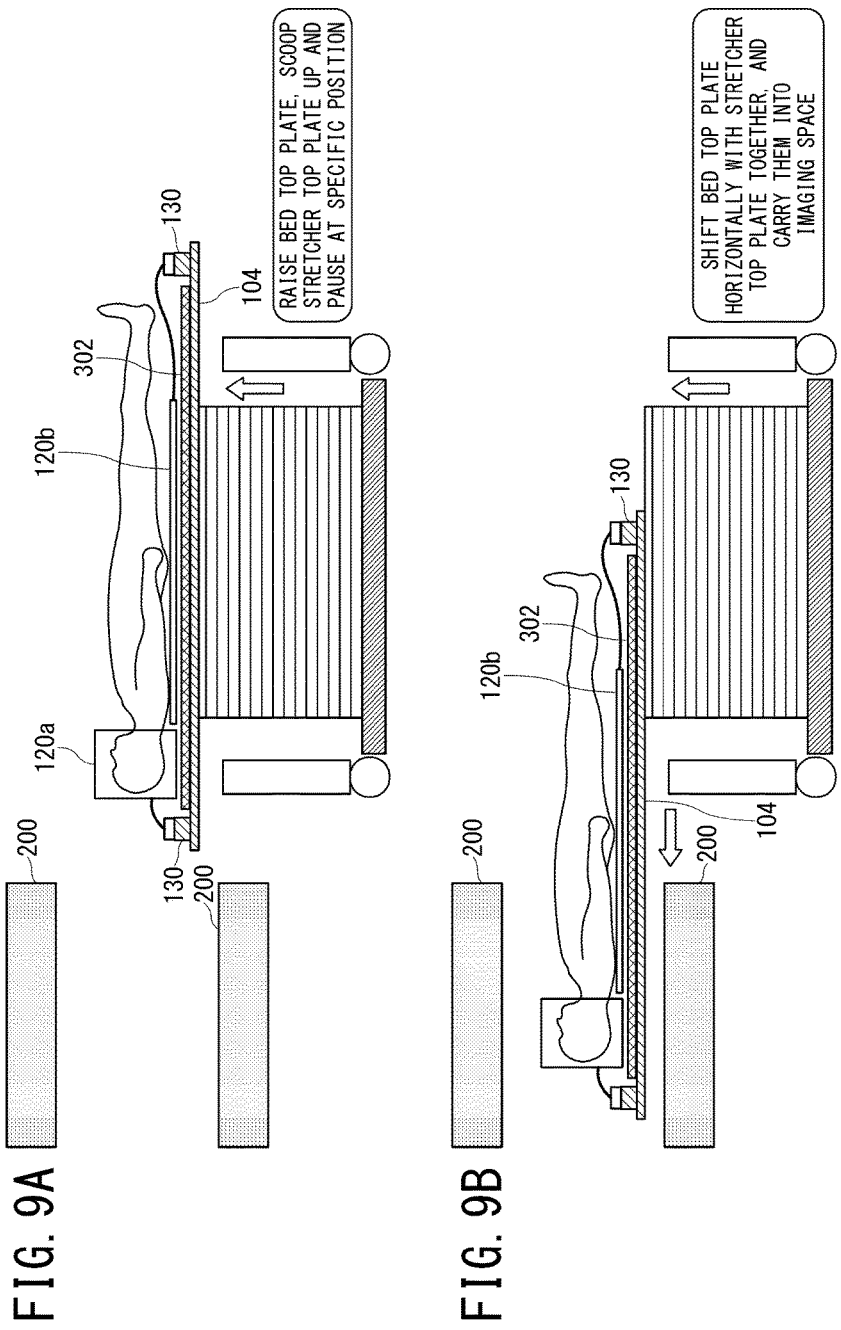

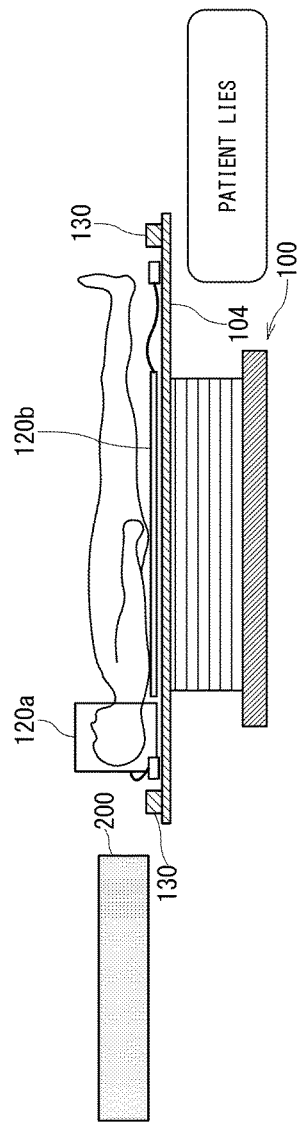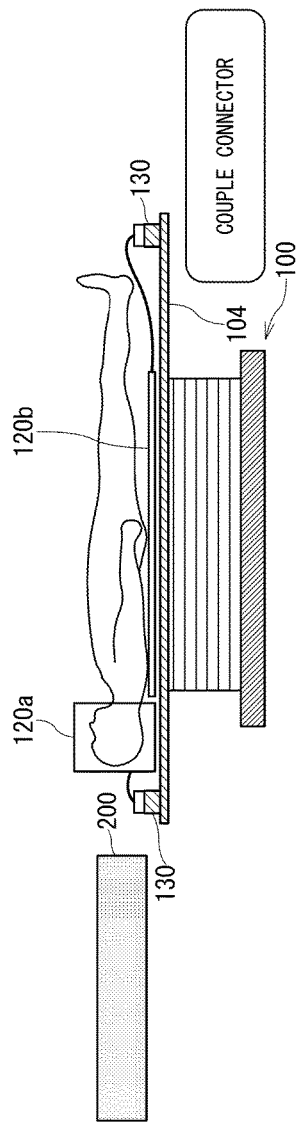

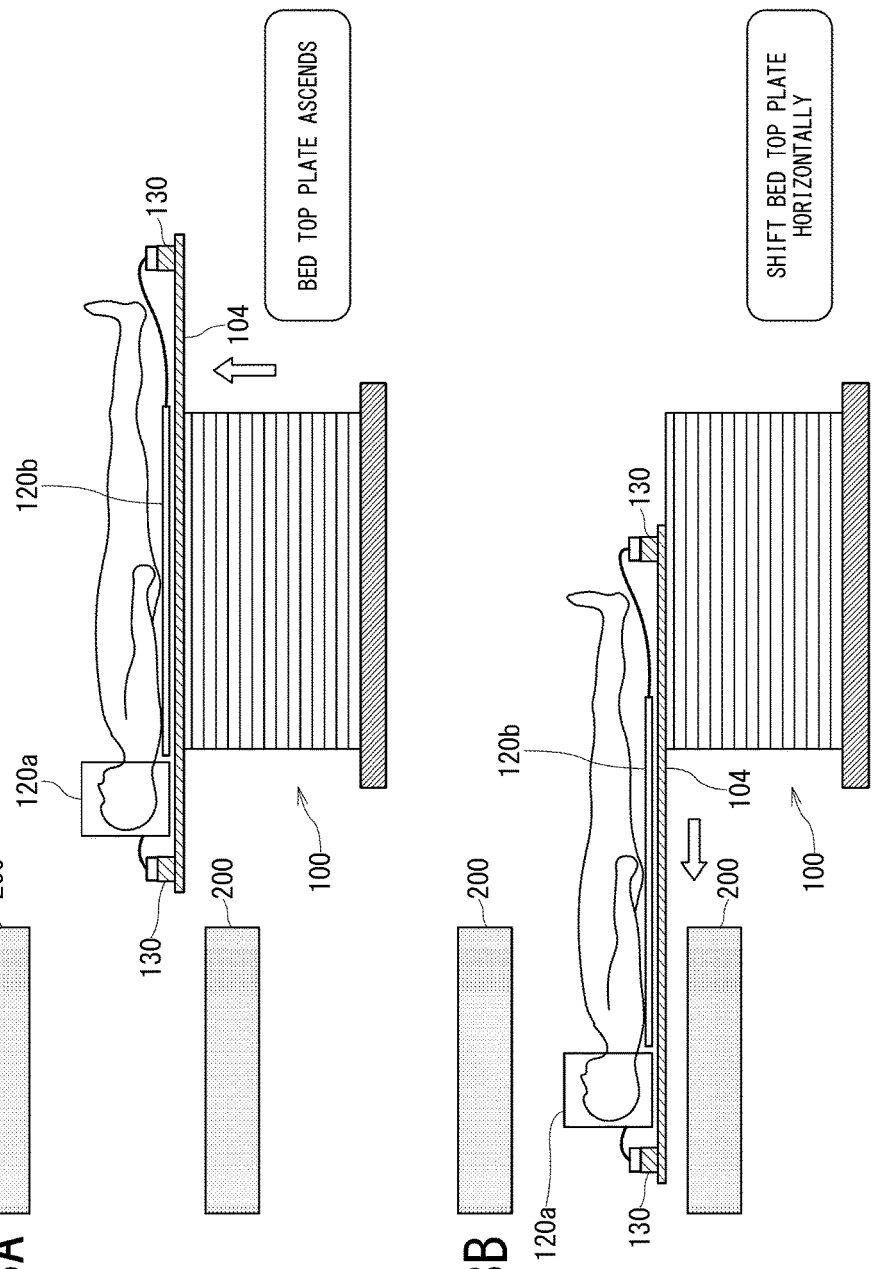

MAGNETIC RESONANCE IMAGING APPARATUS AND METHOD FOR CONTROLLING MAGNETIC RESONANCE IMAGING APPARATUS

CROSS-REFERENCE TO RELATED APPLICATIONS

This application is a Continuation Application of No. PCT/JP2013/81283, filed on Nov. 20, 2013, and the PCT application is based upon and claims the benefit of priority from Japanese Patent Application No. 2012-256782 filed on Nov. 22, 2012, the entire contents of which are incorporated herein by reference.

FIELD

An embodiment of the present invention relates to a magnetic resonance imaging apparatus and a method for controlling the magnetic resonance imaging apparatus.

BACKGROUND

A magnetic resonance imaging apparatus is an apparatus configured to excite a nuclear spin of a test object put in a static magnetic field by an RF (radio frequency) signal of a Larmor frequency, and to reconstruct a magnetic resonance signal generated by the test object as the test object is excited so as to produce an image.

A magnetic resonance imaging apparatus has a gantry and a bed. A cylindrical imaging space is formed in the gantry, and an image of a patient is captured in the imaging space. The bed is arranged next to the gantry, and the patient lies on a top plate provided in an upper portion of the bed before the image is captured. At this time, the top plate has descended to a lower position so that the patient can easily lie. The top plate is movable in a vertical direction, and the vertical shift is performed by a driving mechanism of the bed. In time of imaging, the top plate ascends and then horizontally shifts so as to carry the patient into the imaging space in the gantry. The horizontal shift is performed by the driving mechanism of the bed, as well.

One or a plurality of receiving coils is used for imaging of the patient. The magnetic resonance imaging apparatus has, in lots of recent cases, a connector provided on an end of a cable extended from the receiving coil and a fixed connector provided to the top plate coupled with each other in a removable manner. The bed used in this type of magnetic resonance imaging apparatus includes a plurality of cables laid inside. A signal received by the receiving coil is led, from the fixed connector of the top plate and via the cable inside the bed, to a receiver system provided out of the bed.

For a patient having difficulties in autonomous walking, meanwhile, a stretcher apparatus provided separately from the magnetic resonance imaging apparatus is used as disclosed in Japanese Unexamined Patent Publication No. 2008-12290, etc. The stretcher apparatus is provided with a top plate as well, and the patient is carried into a test room where the magnetic resonance imaging apparatus is installed while lying on the top plate. Then, while the patient is lying on the top plate of the stretcher apparatus, shift the stretcher apparatus to a position where the top plates of the stretcher apparatus and the bed overlap each other. At this time, the top plate of the bed has descended to a low position, and the top plates of the bed and the stretcher apparatus are a certain separation apart. Then, the top plate of the bed ascends and comes into contact with the top plate of the stretcher apparatus. Further, the top plate of the bed ascends as scooping the top plate of the stretcher apparatus up in condition that the top plate of the stretcher apparatus is put on top of the top plate of the bed, and stops at a certain position. Then, the top plate of the bed horizontally shifts, and the top plate of the stretcher apparatus and the patient lying thereon are carried into the imaging space in the gantry together with the top plate of the bed.

The receiving coil is coupled, as described above, with the top plate of the bed (called the bed top plate, hereafter) via the connectors. In the case in which the stretcher apparatus is used, then, the top plate of the stretcher apparatus (called the stretcher top plate, hereafter) comes into contact with the bed top plate when the bed top plate ascends by means of the driving mechanism of the bed, and the top plates are separate from each other when the bed top plate descends.

Thus, if the bed top plate is raised by accident while a receiving coil for the spine remains put on the bed top plate, e.g., the receiving coil and its connection cable may possibly be caught between the bed top plate and the stretcher top plate resulting in being damaged. Further, if a receiving coil for the head or a receiving coil for the abdomen or the chest is fixed to a patient lying on the stretcher top plate and the bed top plate is lowered while such a receiving coil remains coupled with the connector of the bed top plate, the cable of the receiving coil may be possibly pulled downwards as the bed top plate descends resulting in that the receiving coil and the cable are damaged.

Meanwhile, according to an operation ordinarily performed, temporarily stop the ascending operation of the bed top plate shortly before the bed top plate ascends and comes into contact with the stretcher top plate, make sure for safety whether neither an arm nor clothes of the patient are caught between the bed top plate and the stretcher top plate, and then raise the bed top plate again. The above operation assumes a use of the stretcher apparatus. If no stretcher apparatus is used, the temporary stop is unnecessary and is a waste of time.

Thus, a magnetic resonance imaging apparatus which can solve the above problems and a method for controlling such an apparatus are demanded.

SUMMARY

A magnetic resonance imaging apparatus of an embodiment includes: a bed top plate provided with a connector which can be coupled with a receiving coil; a bed which supports the bed top plate, the bed being configured to shift the bed top plate vertically and horizontally, the bed being configured to be jointly coupled with a stretcher apparatus having a stretcher top plate, and the stretcher top plate being placed on top of the bed top plate in a case where the stretcher apparatus is jointly coupled and; a bed controller configured to control a shift of the bed top plate correspondingly to at least one of a joint coupling condition between the bed and the stretcher apparatus and a coupling condition between the receiving coil and the connector.

BRIEF DESCRIPTION OF DRAWINGS

FIGS. 7A and 7B are second diagrams which illustrate a shift operation of the bed in the vertical direction when the stretcher apparatus is used;

FIGS. 8A and 8B are third diagrams which illustrate a shift operation of the bed in the vertical direction when the stretcher apparatus is used;

FIGS. 9A and 9B are fourth diagrams which illustrate a shift operation of the bed in the vertical direction when the stretcher apparatus is used;

FIGS. 12A and 12B are first diagrams which illustrate a shift operation of the bed in the vertical direction when no stretcher apparatus is used;

FIGS. 13A and 13B are second diagrams which illustrate a shift operation of the bed in the vertical direction when no stretcher apparatus is used.

DESCRIPTION OF EMBODIMENTS

An embodiment of the invention will be explained below on the basis of the drawings.

(1) Setup and Overall Operation

Figure 1:
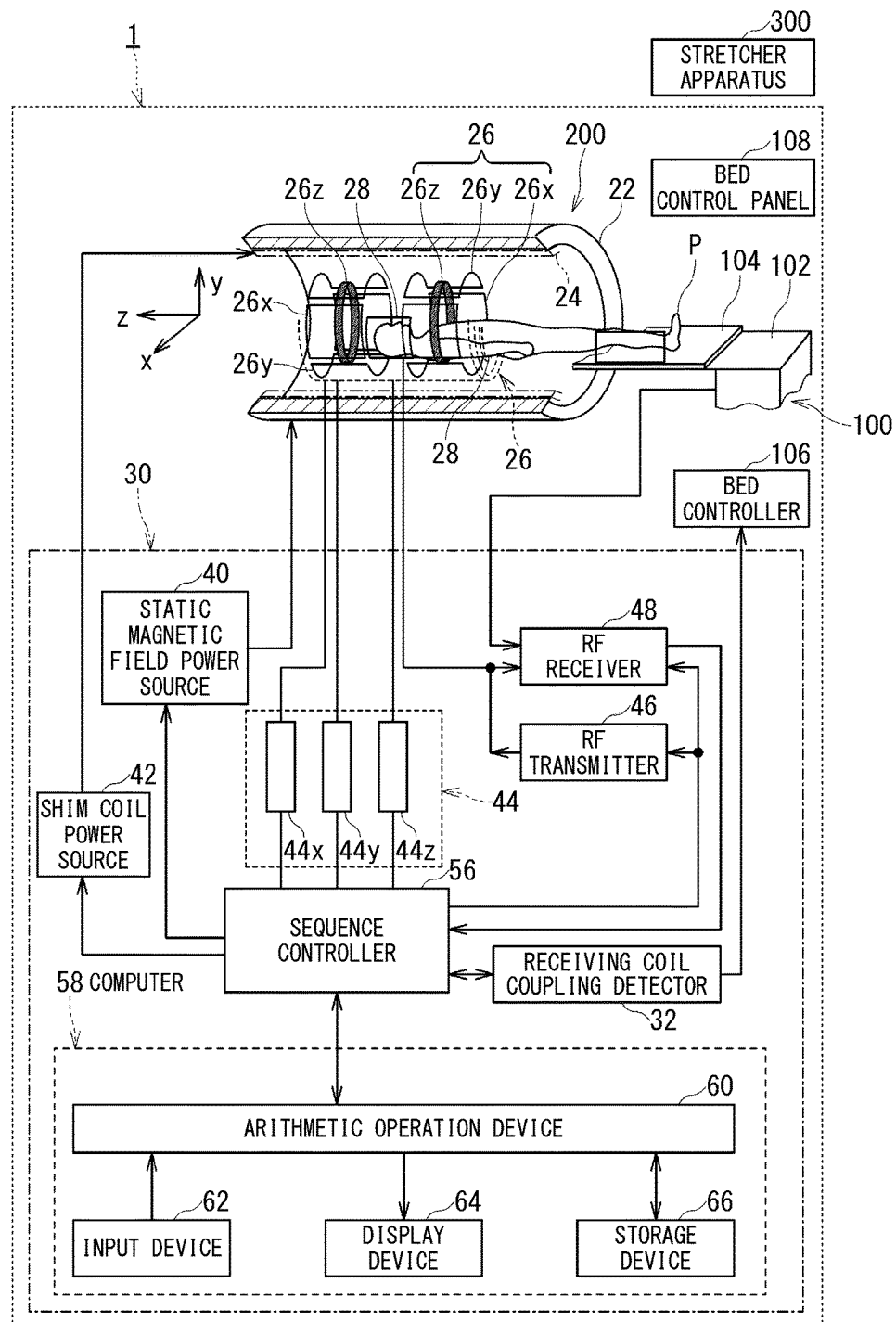
FIG. 1 is a block diagram which depicts an overall setup of a magnetic resonance imaging apparatus 1 of an embodiment.

FIG. 1 is a block diagram which depicts an overall setup of a magnetic resonance imaging apparatus 1 of the embodiment. As depicted in FIG. 1, the magnetic resonance imaging apparatus 1 has a cylindrical magnet for static magnetic fields 22 which forms a static magnetic field, a cylindrical shim coil 24 provided coaxially with and inside the magnet for static magnetic fields 22, a gradient magnetic field coil 26, an RF coil 28 for signal transmission or receiving, a control system 30, a bed 100 on which a test object P (patient) can be mounted, etc. Further, the magnetic resonance imaging apparatus 1 has one or a plurality of receiving coils 120 (including a coil for the head) in addition to a signal transmission/receiving coil for the whole body 28. Still further, the control system 30 has a static magnetic field power source 40, a shim coil power source 42, a gradient magnetic field amplifier unit 44, an RF transmitter 46, an RF receiver 48, a receiving coil coupling detector 32, a sequence controller 56, a computer 58, etc. Further, the computer 58 has an arithmetic operation device 60, an input device 62, a display device 64, a storage device 66, etc., as internal components.

The magnet for static magnetic fields 22 is coupled with the static magnetic field power source 40, and forms a static magnetic field in imaging space by means of a current supplied by the static magnetic field power source 40. The shim coil 24 is coupled with the shim coil power source 42, and levels the static magnetic field off by means of a current supplied by the shim coil power source 42. The magnet for static magnetic fields 22 is formed by a superconductive coil in lots of cases, and is coupled with the static magnetic field power source 40 so as to be supplied with a current in case of being excited. Once being excited, the magnet for static magnetic fields 22 is decoupled in general. Incidentally, the magnet for static magnetic fields 22 may be formed by a permanent magnet without being provided with the static magnetic field power source 40.

The gradient magnetic field coil 26 has an X-axis gradient magnetic field coil 26x, a Y-axis gradient magnetic field coil 26y and a Z-axis gradient magnetic field coil 26z. The gradient magnetic field coil 26 is shaped like a cylinder inside the magnet for static magnetic fields 22.

Figure 2:
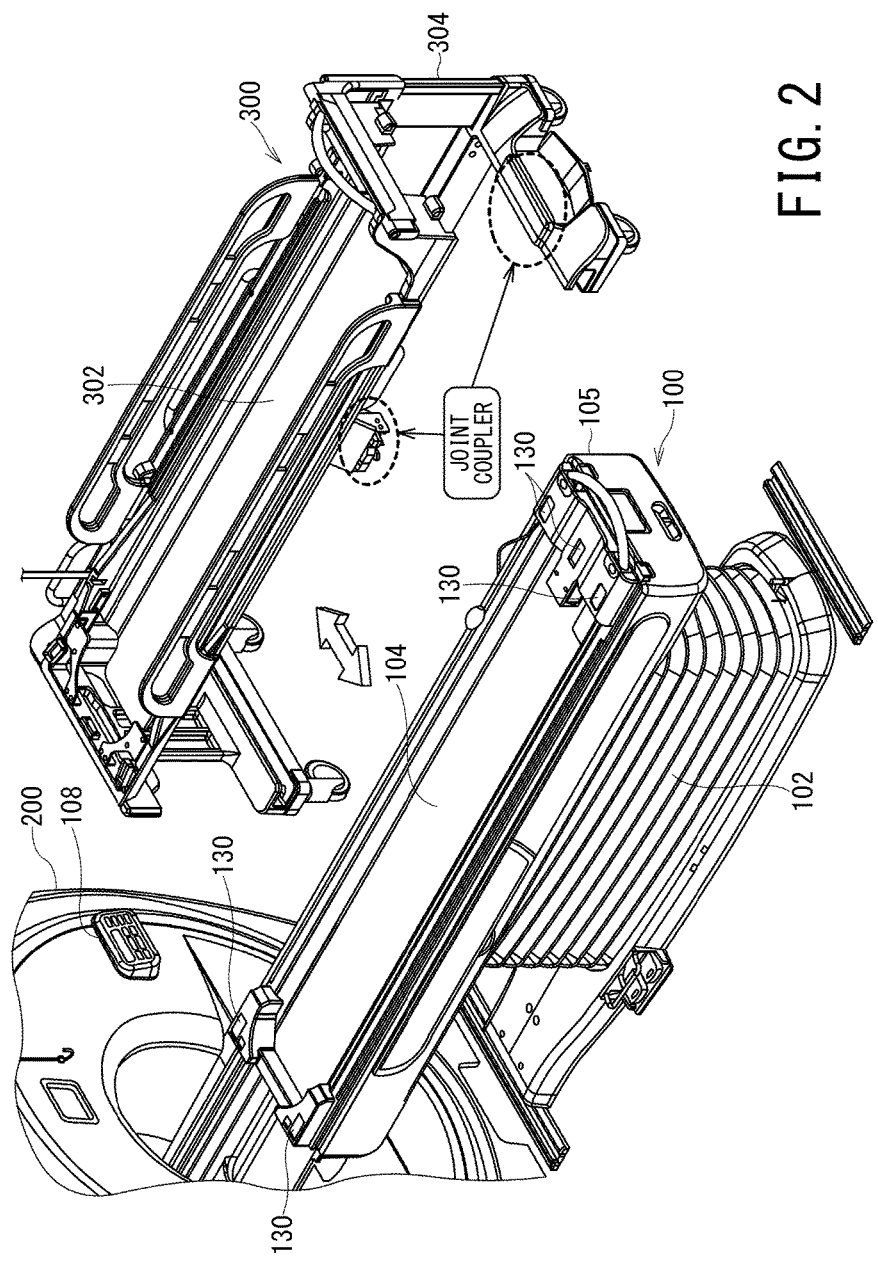
FIG. 2 depicts exemplary perspective views of a bed and a stretcher apparatus which can be jointly coupled with the bed of the embodiment.

The magnet for static magnetic fields 22, the shim coil 24, the gradient magnetic field coil 26, the signal transmission/receiving coil for the whole body 28 and so on are contained in a gantry 200 having a cylindrical imaging space (see FIG. 2).

The gradient magnetic field amplifier unit 44 is formed by an X-axis gradient magnetic field amplifier unit 44x, a Y-axis gradient magnetic field amplifier unit 44y and a Z-axis gradient magnetic field amplifier unit 44z. The X-axis gradient magnetic field coil 26x, the Y-axis gradient magnetic field coil 26y and the Z-axis gradient magnetic field coil 26z are coupled with the X-axis gradient magnetic field amplifier unit 44x, the Y-axis gradient magnetic field amplifier unit 44y and the Z-axis gradient magnetic field amplifier unit 44z, respectively.

The RF transmitter 46 generates an RF pulse of a Larmor frequency for causing a nuclear magnetic resonance on the basis of control information provided by the sequence controller 56, and provides the signal transmission/receiving coil for the whole body 28 (WBC: Whole Body Coil) with the RF pulse.

An MR signal received by the signal transmission/receiving coil for the whole body 28 is provided to the RF receiver 48 via a signal cable. Further, the receiving coil 120 put close to the test object P is coupled with a connector that the bed 100 or the gantry 200 is provided with in a removable manner, and an MR signal received by the receiving coil 120 is provided to the RF receiver 48, as well, via a signal cable provided in the bed 100 or in a housing of the gantry 200.

The RF receiver 48 carries out various kinds of data processing such as pre-amplification, intermediate frequency conversion, phase detection, baseband frequency amplification, filtering and so on for the received MR signal, and then A/D (analog to digital)-converts the MR signal so as to produce raw data which is digitized complex data. The RF receiver 48 provides the sequence controller 56 with the produced raw data of the MR signal.

The sequence controller 56 produces a data sequence and control information for generating gradient magnetic fields Gx, Gy and Gz and an RF pulse which correspond to imaging conditions including a pulse sequence having been set as controlled by the arithmetic operation device 60 in the computer 58, and provides the respective gradient magnetic field amplifier units 44x, 44y and 44z and the RF transmitter 46 with what is produced.

Further, the sequence controller 56 is provided by the RF receiver 48 with an MR signal received in response to the gradient magnetic fields Gx, Gy and Gz and the RF pulse as raw data, and outputs the raw data to the arithmetic operation device 60.

The arithmetic operation device 60 controls the magnetic resonance imaging apparatus 1 entirely, and in addition sets or changes imaging conditions including various kinds of pulse sequences on the basis of information having been provided to the input device and variously set by a user's operation, and controls the sequence controller 56 on the basis of the imaging conditions having been set or changed. Further, the arithmetic operation device 60 carries out a reconstruction process including inverse Fourier transform, etc., for the raw data provided by the sequence controller 56 so as to produce image data.

The arithmetic operation device 60 in the computer 58 is formed by having a processor, etc., and implements the respective functions described above by running program codes stored in the storage device 66.

The magnetic resonance imaging apparatus 1 of the embodiment has the bed 100 which can be jointly coupled with a stretcher apparatus 300, and the bed 100 has a bed main body 102, a bed top plate 104, a bed controller 106, a bed control panel 108 and so on as depicted in FIG. 1.

(2) Structure of the Bed

FIG. 2 gives exemplary appearances of the bed 100 of the embodiment and the stretcher apparatus 300 which can be jointly coupled with the bed 100 in a perspective view.

The bed 100 is placed on a floor, and has a bed main body 102, a bed top plate 104 and a bed supporting portion 105. The bed main body 102 is formed by a bed top plate horizontally driving section 110, a bed top plate vertically driving section 112, a bed controller 106, etc., (see FIG. 4) which are covered by a bellows-like cover material. The bed top plate 104 can be horizontally shifted by the bed top plate horizontally driving section 110. Shift the bed top plate 104 forward (leftward in FIG. 2 called forward) in time of imaging, and carry a patient lying on the bed top plate 104 into the imaging space in the gantry 200. Shift the bed top plate 104 backward (rightward in FIG. 2 called backward) after imaging, and carry the patient out of the imaging space.

FIG. 2 illustrates a condition in which the bed top plate 104 is fully pulled out of the imaging space, and the position of the bed top plate 104 in such a condition is called a home position. When being at the home position in the horizontal direction, the bed top plate 104 can be vertically shifted by the bed top plate vertically driving section 112. Details of a vertical shift (ascending and descending operations) of the bed top plate 104 will be described later.

The bed supporting portion 105 is placed between the bed main body 102 and the bed top plate 104, and supports the bed top plate 104.

The gantry 200 is provided on a side wall with the bed control panel 108, and a user can control shifts of the bed top plate 104 in the horizontal and vertical directions by operating operation buttons, etc., on the bed control panel 108.

The stretcher apparatus 300 is an apparatus for carrying a patient having difficulties in autonomous walking lying thereon. The stretcher apparatus 300 depicted in FIG. 2 is structured to be jointly coupled with the bed 100 of the magnetic resonance imaging apparatus 1, and has a stretcher top plate 302 and a stretcher apparatus main body 304. The stretcher apparatus main body 304 supports the stretcher top plate 302, and can freely move on the floor by means of wheels provided in a lower portion.

The patient is carried into the test room where the magnetic resonance imaging apparatus 1 is installed while lying on the stretcher top plate 302, and the stretcher apparatus 300 is placed in such a way that long side directions of the stretcher top plate 302 and the bed top plate 104 are substantially parallel to each other. The stretcher apparatus main body 304 is substantially shaped like a rectangle having one open side as viewed from back to front, and is open on the side facing the bed 100. Thus, if the bed top plate 104 is lowered to a certain position, the stretcher apparatus 300 can be shifted to a position where the stretcher top plate 302 is put on top of the bed top plate 104 as covering the bed top plate 104 over (in the direction of a block arrow symbol depicted in FIG. 2).

The stretcher apparatus main body 304 is provided at positions indicated with dashed ellipses in a lower portion with joint couplers for being jointly coupled with the bed 100. The stretcher apparatus 300 and the bed 100 are jointly coupled and fixed with each other at a position where the stretcher top plate 302 and the bed top plate 104 are put on top of each other.

The stretcher top plate 302 is, meanwhile, just put on the stretcher apparatus main body 304, and the stretcher top plate 302 is not fixed with the stretcher apparatus main body 304. Thus, upon being raised, the bed top plate 104 scoops the stretcher top plate 302 up after the upper face of the bed top plate 104 comes into contact with the lower face of the stretcher top plate 302. Then, the bed top plate 104 and the stretcher top plate 302 ascend while being in contact with each other, i.e., a double-layered top plate, and stop at a position where they can be carried into the imaging space in the gantry 200. Then, if the bed top plate 104 is horizontally shifted, the stretcher top plate 302 is carried into the imaging space in the gantry 200 with the bed top plate 104 together.

The patient having been carried to the test room by the stretcher apparatus 300 is carried into the imaging space in the gantry 200 while keeping lying on the stretcher top plate 302 in this way. The patient is carried outwards in an opposite order after an imaging operation. The patient is pulled out of the imaging space while keeping lying on the stretcher top plate 302. After the bed top plate 104 descends, then, the stretcher top plate 302 is separate from the bed top plate 104 and is received by the stretcher apparatus main body 304. After the joint coupling between the stretcher apparatus 300 and the bed 100 is released, the patient is carried out of the test room still by the stretcher apparatus 300.

The magnetic resonance imaging apparatus 1 can use a plurality of receiving coils 120 as described above. The receiving coils 120 are prepared for respective anatomic portions to be imaged, and includes a head coil 120a, a spine coil 120b, and a body coil 120c, etc.

One of them, the spine coil 120b, is laid on the bed top plate 104 or the stretcher top plate 302 before the patient lies in a supine posture above the spine coil 120b.

Meanwhile, the bed top plate 104 is provided on front and back positions with a plurality of connectors 130 to be coupled with the plural receiving coils 120.

Figure 3:
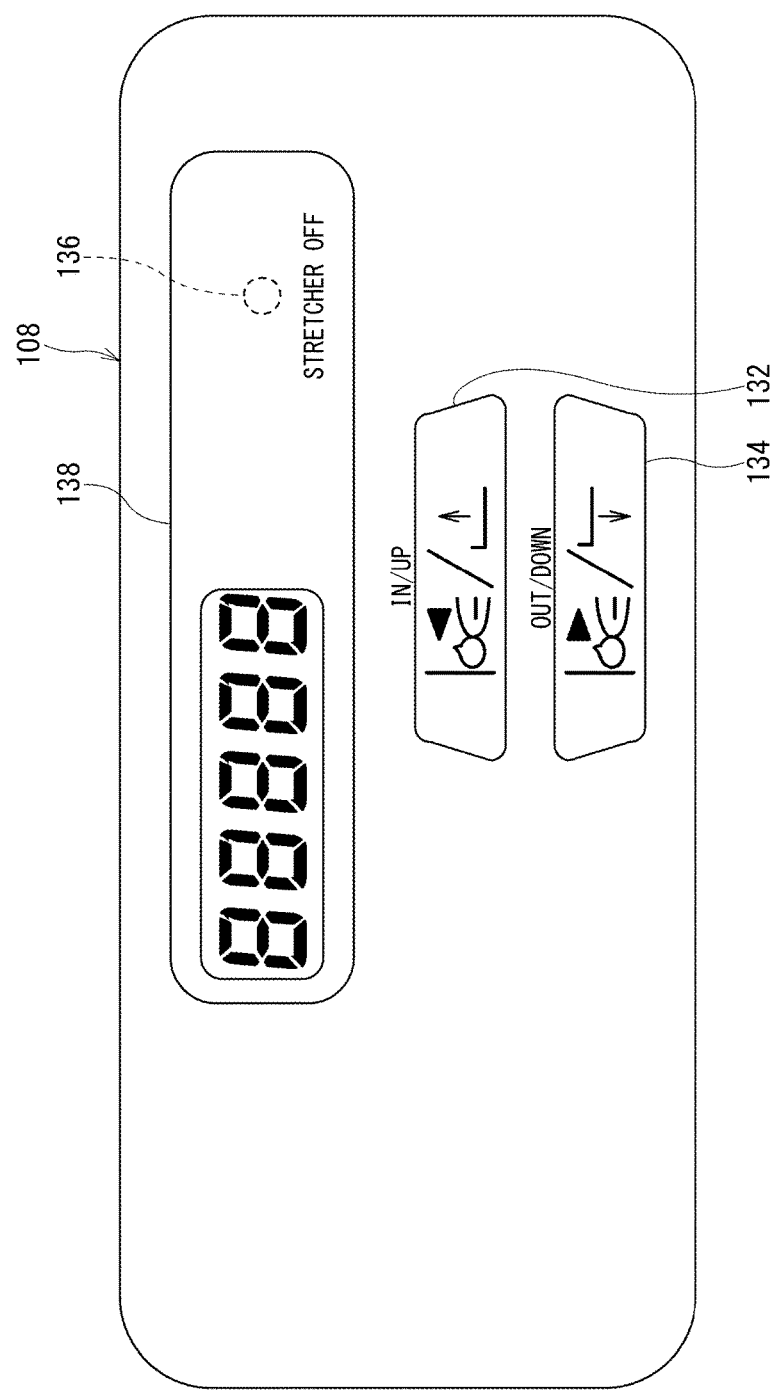
FIG. 3 illustrates an exemplary arrangement of operation parts on a bed control panel.

FIG. 3 illustrates an exemplary arrangement of operation buttons, etc., on the bed control panel 108 provided on the side wall of the gantry 200. The bed control panel 108 has an "up" button 132 for raising the bed top plate 104 and a "down" button 134 for lowering the bed top plate 104. The "up" button 132 serves as well as a "carry-in" button for carrying the bed top plate 104 inwards, and the "down" button 134 serves as well as a "carry-out" button for carrying the bed top plate 104 outwards. The bed control panel 108 further has a "stretcher off" lamp 136 which indicates joint coupling condition between the bed 100 and the stretcher apparatus 300, and a monitor display 138 which indicates an error code, etc.

Figure 4:
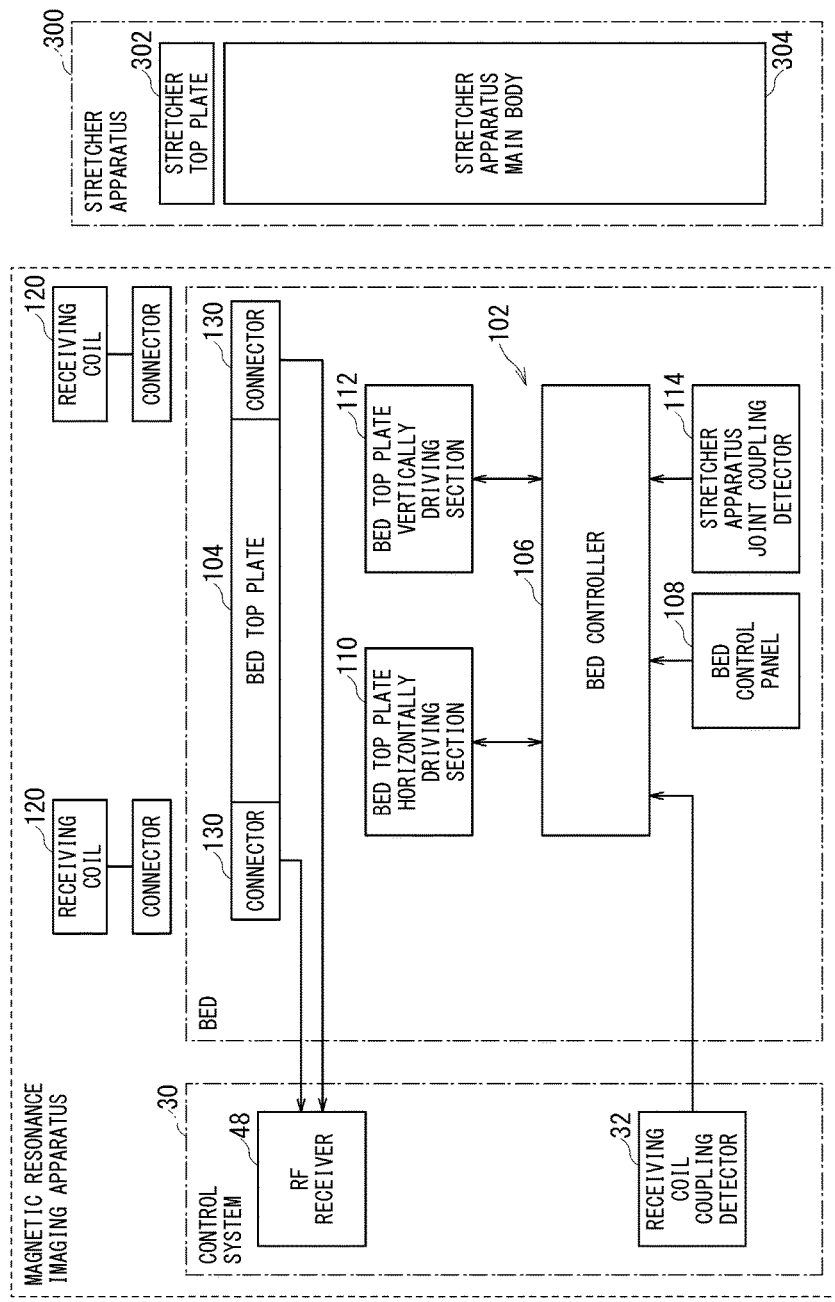
FIG. 4 depicts a functional block diagram of the bed.

FIG. 4 depicts a functional block diagram related to an operation of the bed 100. As described above, the bed 100 has the bed main body 102, the bed top plate 104 and the bed supporting portion 105. The bed main body 102 has the bed top plate horizontally driving section 110, the bed top plate vertically driving section 112 and the bed controller 106. The bed controller 106 implements various kinds of functions described later by means of a processor which is not depicted and a software component. The functions of the bed controller 106 can be implemented by means of a hardware component instead of the software component, or of a combination of software and hardware components.

The bed top plate 104 has a plurality of the connectors 130, and two of them are depicted in FIG. 4. The connector 130 is coupled with the receiving coil 120. More specifically, a coil-linked connector put to an end of a cable extended from each of the receiving coils 120 is coupled with the connector 130 on the bed top plate 104.

When the receiving coil 120 is coupled with the connector 130 on the bed top plate 104, a control signal indicating a type of the receiving coil 120, etc., reaches the receiving coil coupling detector 32 via the RF receiver 48 in the controller 30 of the magnetic resonance imaging apparatus 1. The receiving coil coupling detector 32 can detect coupling condition of coupling and decoupling between the receiving coil 120 and the connector 130 on the bed top plate 104 on the basis of the control signal. The coupling condition between the receiving coil 120 and the connector 130 is transmitted to the bed controller 106 in the bed 100.

As for the joint coupling condition between the stretcher apparatus 300 and the bed 100, meanwhile, the bed 100 has a stretcher apparatus joint coupling detector 114 which detects the joint coupling condition between the stretcher apparatus 300 and the bed 100 by means of a micro switch, etc.

The bed controller 106 of the embodiment controls driving of the bed top plate 104 in the vertical direction on the basis of a signal of user's operation on the bed control panel 108, and in addition the joint coupling condition between the stretcher apparatus 300 and the bed 100, and the coupling condition between the receiving coil 120 and the connector 130. An operation of the bed 100 including the driving control in the vertical direction will be explained below.

(3) Operation of the Bed (First Embodiment)

Figure 5:
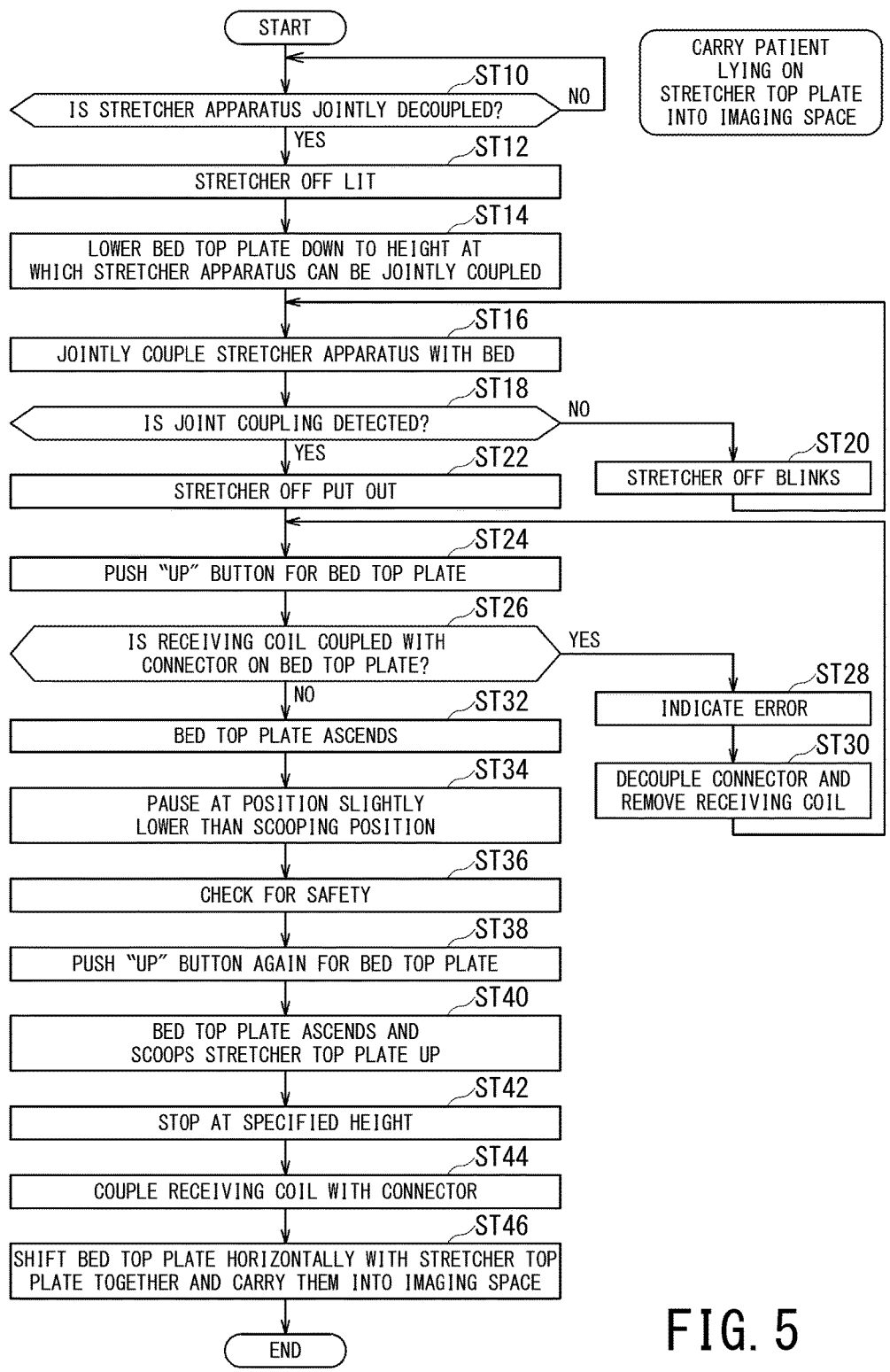
FIG. 5 is a flowchart which illustrates an exemplary operation (in time of carrying into the imaging space) of a bed of a magnetic resonance imaging apparatus of a first embodiment.

An operation of the bed 100 of a first embodiment is an operation of the bed 100 in a case where the stretcher apparatus 300 is used. FIG. 5 is a flowchart which illustrates an exemplary operation up until a patient lying on the stretcher top plate 302 is carried into the imaging space in the gantry 200. Further, FIGS. 6-9 each illustrate the operation related to the flowchart of FIG. 5.

Figure 6:
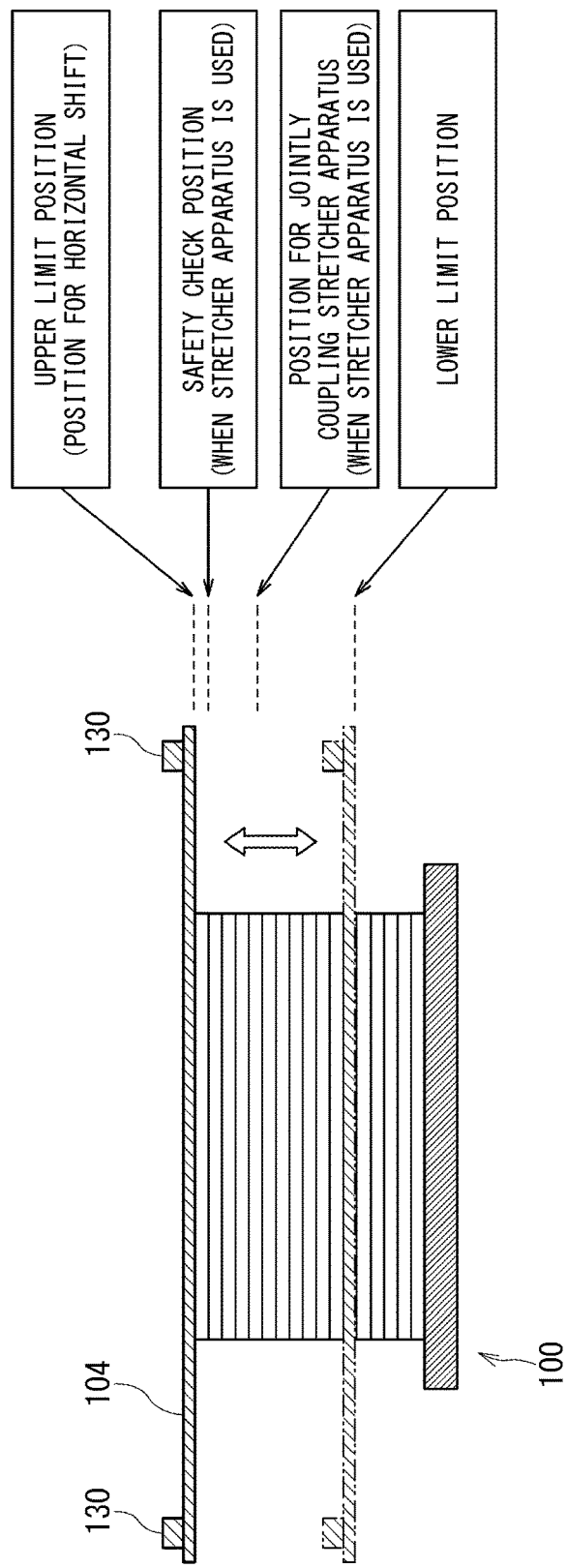
FIG. 6 is a first diagram which illustrates a shift operation of the bed in the vertical direction when the stretcher apparatus is used.

FIG. 6 exemplarily illustrates positions where the bed top plate 104 stops in the vertical direction. The lower limit position is where the bed top plate 104 has descended to the lowest. In a case where no stretcher apparatus 300 is used, shift the bed top plate 104 to the lower limit position and have a patient lie on the bed top plate 104. Meanwhile, the upper limit position is where the bed top plate 104 has ascended to the highest. After raising the bed top plate 104 up to this position, usually, shift the bed top plate 104 horizontally so as to carry the patient into or out of the imaging space.

In contrast, the bed top plate 104 pauses, when the stretcher apparatus 300 is used, at a stretcher apparatus joint coupling position and a safety check position.

The flowchart depicted in FIG. 5 supposes, initially, that the bed top plate 104 is at the higher limit position as depicted in FIG. 7A, and that the stretcher apparatus 300 is not jointly coupled with the bed 100. The patient is carried into the test room while lying on the stretcher top plate 302 of the stretcher apparatus 300 as depicted in FIG. 7B. When the spine coil 120b is used, let the patient lie at this moment above the spine coil 120b having been laid on the stretcher top plate 302 in advance. Further, when the head coil 120a is used, it can be fit to the patient's head on the stretcher top plate 302 as depicted in FIG. 7B.

The joint coupling condition between the stretcher apparatus 300 and the bed 100 is monitored at a step ST10 in FIG. 5, and the "stretcher off" lamp 136 is being lit (step ST12) unless they are jointly coupled (YES of step ST10). Then, push the "down" button 134 so as to lower the bed top plate 104 down to a height at which the stretcher apparatus 300 can be jointly coupled (step ST14).

Then, shift the stretcher apparatus 300 and jointly couple the stretcher apparatus 300 with the bed 100 (step ST16). When the stretcher apparatus joint coupling detector 114 detects a joint coupling (YES of step ST18), the "stretcher off" lamp 136 is put out (step ST22). Meanwhile, if the joint coupling is uncertain, e.g., only one of the two joint couplers is jointly coupled (NO of step ST18), the "stretcher off" lamp 136 blinks (step ST20) so as to draw a user's attention.

FIG. 8A schematically illustrates an end of the joint coupling between the stretcher apparatus 300 and the bed 100 due to data processing up to the step ST22.

Then, if the user pushes the "up" button 132 on the bed control panel 108 (step ST24), the bed controller 106 checks coupling condition between the receiving coil 120 and the connector 130 on the bed top plate 104 before starting an ascending operation (step ST26).

According to a regular and correct operation procedure, it is supposed to connect the receiving coil 120 after the bed top plate 104 ascends up to the higher limit position. Thus, what is meant by a fact that a coupling between the receiving coil 120 and the connector 130 is detected in the phase of the step ST26 is that the receiving coil 120 is probably left on the bed top plate 104 by accident. Thus, if a coupling between the receiving coil 120 and the connector 130 (YES of step ST26) is detected, the bed controller 106 of the embodiment indicates an error without raising the bed top plate 104 (step ST28). The error indication is performed by a certain error code displayed on the display monitor 138 on the bed control panel 108, etc.

The user checks whether the receiving coil 120 is left between the bed top plate 104 and the stretcher top plate 302 on the basis of the error indication, and removes the receiving coil 120 if it is left (step ST30). Then, return to the step ST24 and push the "up" button 132 again.

If the receiving coil 120 is decoupled from the connector 130 (YES of step ST26), the bed top plate 104 ascends (step ST32) and pauses at a safety check position being slightly lower than a scooping position (step ST34) (see FIG. 8B).

The user such as an imaging operator can check for safety whether neither a finger nor clothes of the patient are caught between the bed top plate 104 and the stretcher top plate 302 by giving a pause in the ascent of the bed top plate 104 at the safety check position (step ST36).

If the safety check is satisfactory, push the "up" button 132 again (step ST38) so as to resume raising the bed top plate 104. Then, the upper face of the bed top plate 104 comes into contact with the lower face of the stretcher top plate 302, and the bed top plate 104 scoops the stretcher top plate 302 up and ascends (step ST40), and stops at the specified upper limit position (step ST42) (see FIG. 9A).

When the bed top plate 104 stops at the specified upper limit position, the user couples the receiving coil 120 with the connector 130 on the bed top plate 104 (step ST44).

Then, shift the bed top plate 104 backwards in the horizontal direction with the stretcher top plate 302 on which the patient is lying together by operating the bed control panel 108 so as to carry them into the imaging space in the gantry (step ST46) (see FIG. 9B).

According to the operation described above, even if the "up" button 132 is pushed while the receiving coil 120 having been left remains on the bed top plate 104, the bed top plate 104 does not ascend so that the receiving coil 120 having been left can be prevented from being caught between the bed top plate 104 and the stretcher top plate 302 and damaged.

Figure 10:
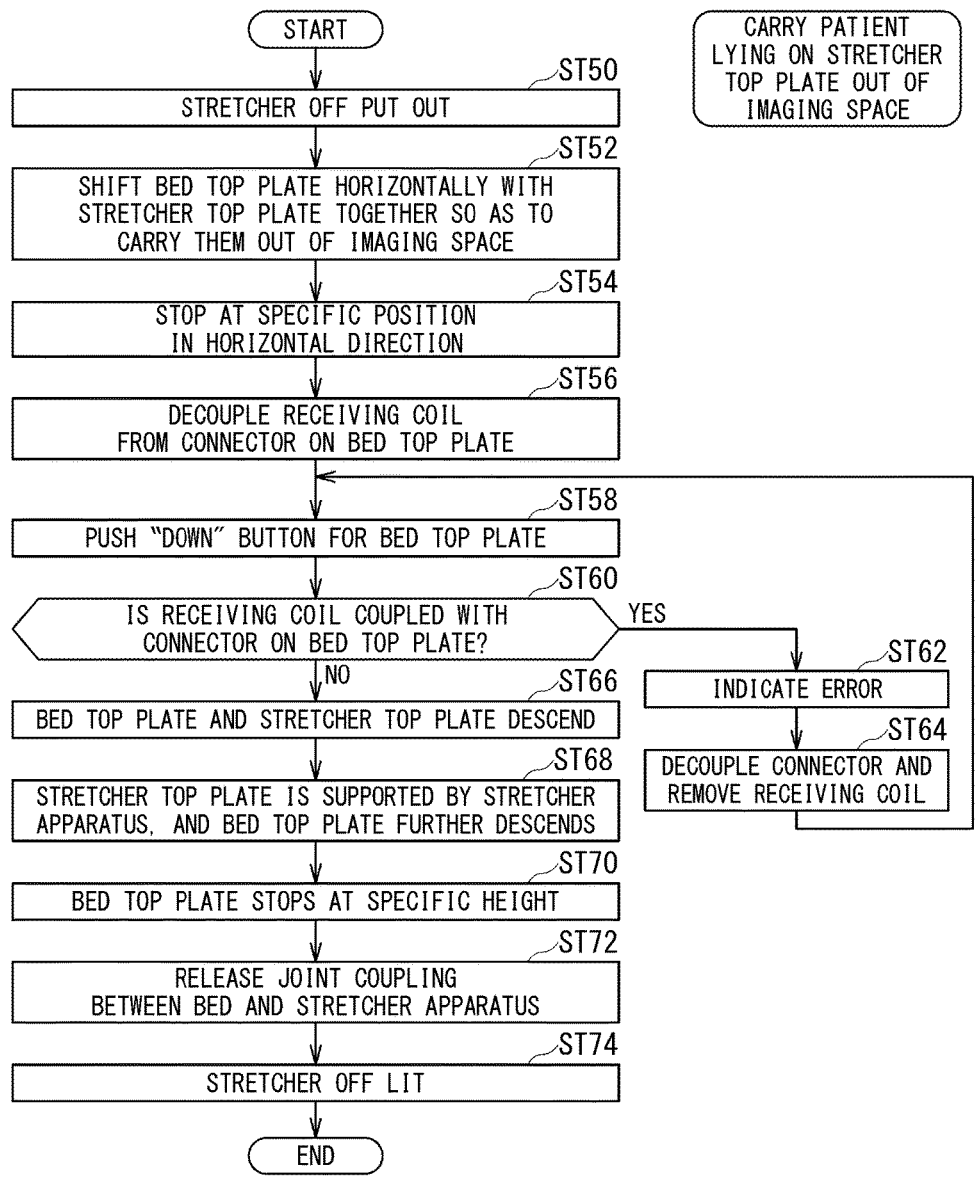
FIG. 10 is a flowchart which illustrates an exemplary operation (in time of carrying out of the imaging space) of the bed of the magnetic resonance imaging apparatus of the first embodiment.

FIG. 10 is a flowchart which indicates a flow of an operation to carry the patient out of the imaging space. As the stretcher apparatus 300 remains jointly coupled with the bed 100 during the imaging operation, the "stretcher off" lamp 136 remains put out (step ST50). If the imaging operation ends, the user (the imaging operator, etc.) operates the bed control panel 108 so as to horizontally shift the bed top plate 104 with the stretcher top plate 302 on which the patient is lying together, and to carry the patient out of the imaging space (step ST52). The bed top plate 104 stops at a specified position in the horizontal direction (the upper limit position in the vertical direction) (step ST54). The user disconnects the receiving coil 120 from the connector 130 on the bed top plate 104 at this position (step ST56).

Then, when the user pushes the "down" button 134 on the bed control panel 108 (step ST58), the bed controller 106 checks the coupling condition between the receiving coil 120 and the connector 130 on the bed top plate 104 before starting a descending operation (step ST60).

According to the regular and correct operation procedure, it is supposed to disconnect the receiving coil 120 while the bed top plate 104 remains at the higher limit position. Thus, what is meant by a fact that a coupling between the receiving coil 120 and the connector 130 is detected in the phase of the step ST60 is that the disconnection of the receiving coil 120 from the connector 130 is forgotten for at least one of the receiving coils 120. Thus, if a coupling between the receiving coil 120 and the connector 130 is detected (YES of step ST60), the bed controller 106 of the embodiment indicates an error without lowering the bed top plate 104 (step ST62). The error indication is performed, similarly as at the step ST28 in FIG. 5, by a certain error code displayed on the display monitor 138 on the bed control panel 108, etc.

The user checks whether no disconnection of the receiving coil 120 is forgotten on the basis of the error indication, and disconnects the receiving coil 120 forgotten being disconnected, if any, from the connector 130 (step ST64). Then, return to the step ST58 and push the "down" button 134 again.

Unless the receiving coil 120 is coupled with the connector 130 (NO of step ST60), the bed top plate 104 and the stretcher top plate 302 start descending (step ST66). While the stretcher top plate 302 comes into contact with a supporting member of the stretcher apparatus main body 304 on the way of descending and stops at that position, the bed top plate 104 continues descending (step ST68). Then, the bed top plate 104 stops at a certain height (the stretcher apparatus joint coupling position or the lower limit position depicted in FIG. 6) (step ST70).

Then, when the user releases the joint coupling between the bed 100 and the stretcher apparatus 300, the stretcher apparatus joint coupling detector 114 detects that fact, and the "stretcher off" lamp 136 on the bed control panel 108 is lit.

According to the operation described above, even if the "down" button 134 is pushed while the receiving coil 120 remains coupled with the bed top plate 104, the bed top plate 104 does not descend. Thus, matters such that a cable of the receiving coil 120 being fit to the patient on the stretcher top plate 302 is pulled as the bed top plate 104 descends resulting in that the cable of the receiving coil 120 or the receiving coil 120 is damaged can be prevented from occurring. Further, as the error indication indicates that the receiving coil 120 is coupled with the connector 130, the user can be immediately aware of the receiving coil 120 forgotten being disconnected and can properly deal with that.

(4) Operation of the Bed (Second Embodiment)

Figure 11:
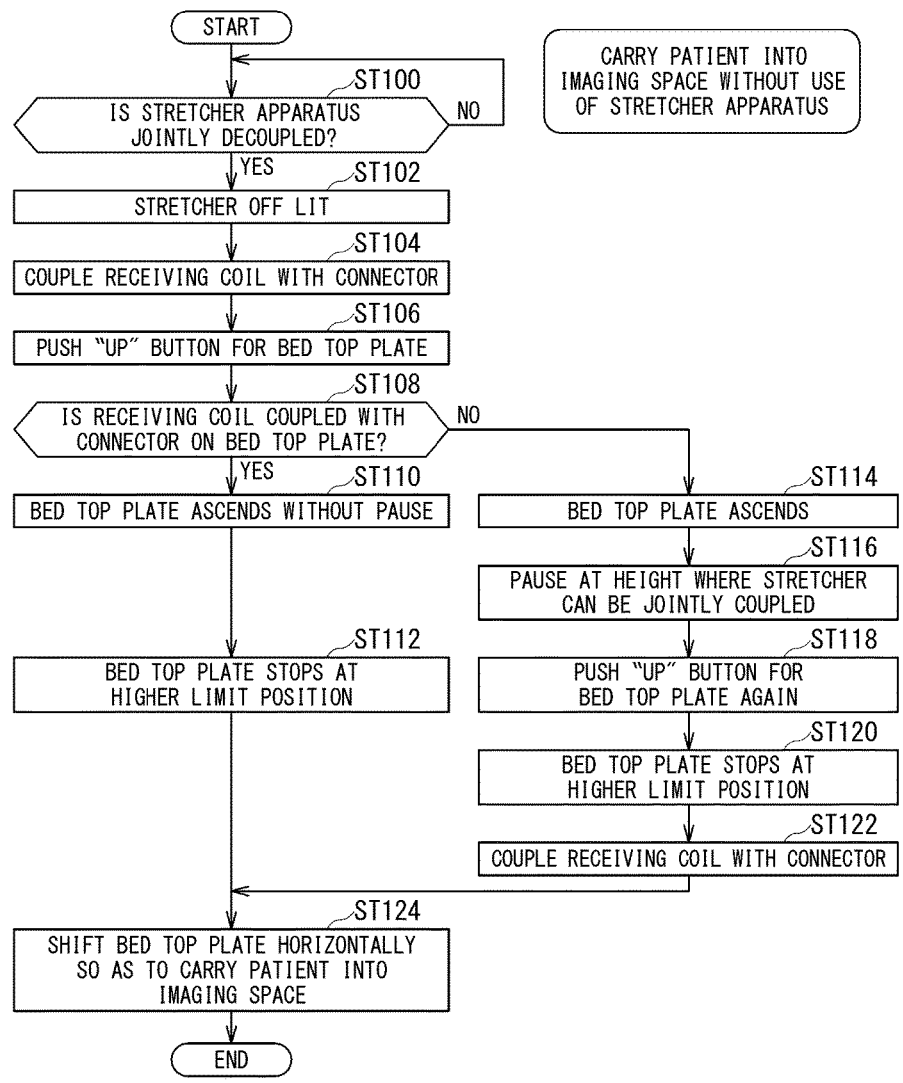
FIG. 11 is a flowchart which illustrates an exemplary operation (in time of carrying into the imaging space) of a bed of a magnetic resonance imaging apparatus of a second embodiment.

An operation of the bed 100 of a second embodiment is an operation of the bed 100 in a case where the stretcher apparatus 300 is not used. FIG. 11 is a flowchart which illustrates, in the above, an exemplary operation up until a patient lying on the bed top plate 104 is carried into the imaging space in the gantry 200. Further, FIGS. 12 and 13 each illustrate the operation described above.

The joint coupling condition between the stretcher apparatus 300 and the bed 100 is monitored at a step ST100 in FIG. 11, and the "stretcher off" lamp 136 is lit (step ST102) in case of no joint coupling (YES of step ST100).

When the stretcher apparatus 300 is not used, the bed top plate 104 is lowered down to a position that a patient can conveniently lie on, e.g., the lower limit position, and the patient lies on the bed top plate 104 at this position (see FIG. 12A).

Then, the user couples the receiving coil 120 with the connector 130 on the bed top plate 104 (step ST104) (FIG. 12B).

Then, when the user pushes the "up" button 132 on the bed control panel 108 (step ST106), the bed controller 106 checks a coupling between the receiving coil 120 and the connector 130. If a coupling between the receiving coil 120 and the connector 130 is identified (YES of step ST108), the bed controller 106 raises the bed top plate 104 up to the higher limit position without a pause on the way (step ST110), and stops the bed top plate 104 at the higher limit position (step ST112) (FIG. 13A). Then, shift the bed top plate 104 in the horizontal direction by operating the bed control panel 108 so as to carry the patient into the imaging space (step ST124) (FIG. 13B).

If no coupling between the receiving coil 120 and the connector 130 is identified (NO of step ST108), on the other hand, start an ascent of the bed top plate 104 (step ST114), and then make a pause at the stretcher apparatus joint coupling position (step ST116). Then, when the user pushes the "up" button 132 again (step ST118), the bed top plate 104 restarts ascending and stops at the upper limit position (step ST120). Then, couple the receiving coil 120 with the connector 130 (step ST122), and go forward to a step ST124.

Figure 14:
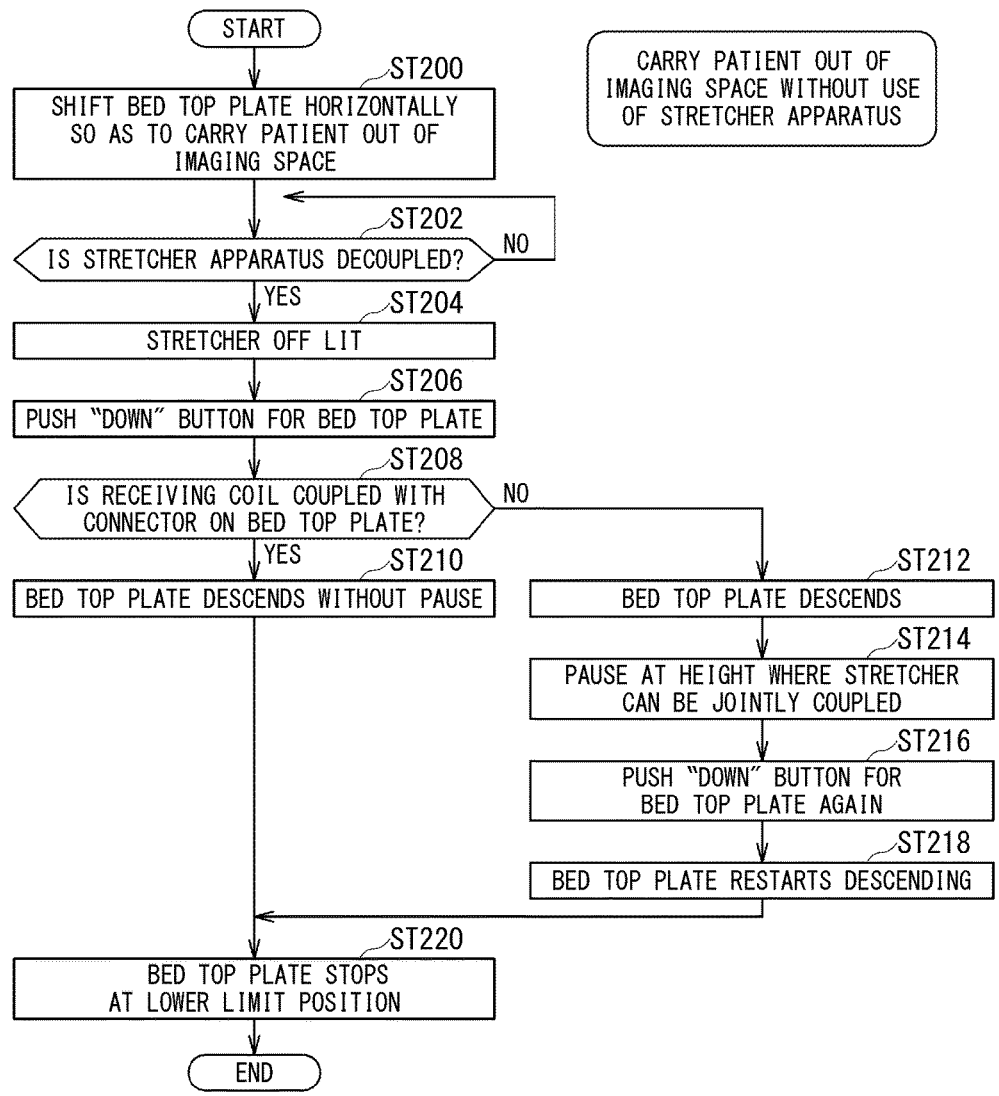
FIG. 14 is a flowchart which illustrates an exemplary operation (in time of carrying out of the imaging space) of the bed of the magnetic resonance imaging apparatus of the second embodiment.

FIG. 14 is a flowchart which illustrates an exemplary operation to carry a patient out of the imaging space in a case where the stretcher apparatus 300 is not used.

The patient is carried out of the imaging space at a step ST200. Further, the joint coupling condition between the stretcher apparatus 300 and the bed 100 is monitored, and the "stretcher off" lamp 136 is being lit (step ST204) in case of no joint coupling (YES of step ST202).

When the "down" button 134 on the bed control panel 108 is pushed in this condition (step ST206), the bed controller 106 checks a coupling between the receiving coil 120 and the connector 130. If a coupling between the receiving coil 120 and the connector 130 is identified (YES of step ST208), the bed controller 106 lowers the bed top plate 104 down to the lower limit position without a pause on the way (step ST210), and stops the bed top plate 104 at the lower limit position (step ST220).

Unless a coupling between the receiving coil 120 and the connector 130 is identified (NO of step ST208), on the other hand, start a descent of the bed top plate 104 (step ST212), and then make a pause at the stretcher apparatus joint coupling position (step ST214). Then, when the "down" button 134 is pushed again (step ST216), the bed top plate 104 restarts descending (step ST218) and stops at the lower limit position (step ST220).

If the bed controller 106 detects no joint coupling between the stretcher apparatus 300 and the bed 100, i.e., an imaging operation is done without a use of the stretcher apparatus 300, and if the receiving coil 120 is already coupled with the connector 130, according to the second embodiment described above, the bed controller 106 shifts the bed top plate 104 in the vertical direction from the lower limit position to the upper limit position or from the upper limit position to the lower limit position without a pause on the way.

A period of time for a pause is thereby saved, and further no operation to restart an ascent or a descent is required, and thus efficiency of shift operations of the bed top plate 104 in the vertical direction is improved.

According to the magnetic resonance imaging apparatus 1 of the embodiment, as described above, a cable of the receiving coil 120 or the receiving coil 120 can be prevented from being damaged if the stretcher apparatus 300 is used, and shifts of the bed top plate 104 in the vertical direction can be done in a lossless and efficient manner.

The control of the shifts of the bed top plate 104 in the vertical direction are explained as to the embodiments described above. However, it is practical as well to control shifts of the bed top plate 104 in the horizontal direction in addition to or instead of the vertical direction, in accordance with the coupling condition between the receiving coil 120 and the connector 130, the position of the connector 130 to be coupled with the receiving coil 120, the type of the receiving coil 120 or a joint coupling condition of the stretcher apparatus 300. In a case where, e.g., a wrong receiving coil 120 never to be coupled is coupled with the connector 130, a receiving coil 120 to be rightfully coupled is decoupled from the connector 130, etc., forbid or restrict a shift of the bed top plate 104 in the horizontal direction so as to prevent an operation to carry a patient inwards, etc., from being redone. Further, in a case where the bed 100 is provided on the front and rear sides with connectors 130, e.g., it is practical as well to forbid or restrict a shift of the bed top plate 104 in the horizontal direction if a receiving coil 120 to be rightfully coupled with the front connector 130 is coupled with the rear connector 130, or if a receiving coil 120 to be rightfully coupled with the rear connector 130 is conversely coupled with the front connector 130.

Further, when the stretcher apparatus 300 is to be jointly coupled, a position of the stretcher top plate 302 on which a patient lies may be higher than a regular position of the bed top plate 104. Thus, if a receiving coil 120 larger than usual is used, the receiving coil 120 may conceivably mechanically interfere with an upper portion of a bore (imaging space in the gantry) when a patient is carried into the bore. In such a case, the gantry or the receiving coils can be prevented from being damaged upon a shift of the bed top plate 104 in the horizontal direction being forbidden or restricted in accordance with a coupling condition between the receiving coil 120 and the connector 130 or a joint coupling condition of the stretcher apparatus 300. If the bed 100 is provided both on the front and rear sides with connectors 130 which each can be coupled with the receiving coil 120, and if the receiving coil 120 being coupled with the front connector 130 interferes with the upper portion of the bore, e.g., it is practical as well to allow the bed top plate 104 to shift in the horizontal direction only if the receiving coil 120 is coupled with the rear connector 130.

Further, although it is supposed to couple a receiving coil 120 with a connector 130 on the bed top plate 104 as to the embodiments described above, the position of the connector to be coupled with the receiving coil 120 is not limited to on the bed top plate 104. It is practical as well, e.g., to provide an area on the side wall of the gantry 200 with a connector to be coupled with the receiving coil 120 in another setup.

The embodiments of the invention having been explained are presented as exemplary only, and it is not intended to limit the scope of the invention. These embodiments can be practiced in other various forms, and can be variously omitted, replaced or changed within the gist of the invention. The inventions and their modifications are included in the scope and the gist of the invention, and in the inventions described in the claims and their equivalents as well.

What is claimed is:

1. A magnetic resonance imaging (MRI) apparatus comprising:
   a radio frequency (RF) MR signal receiving coil;
   a bed top plate configured to support an object to be imaged, said bed top plate being provided with a connector thereon, the connector being configured to be coupled with the RF MR signal receiving coil;
   a bed structure which supports the bed top plate, the bed structure being configured to shift the bed top plate vertically and horizontally so as to position the object to be imaged within an imaging volume of an MRI system, the bed structure being configured to be jointly coupled with a stretcher apparatus having a stretcher top plate, and the stretcher top plate being placed on top of the bed top plate when the stretcher apparatus is jointly coupled with the bed structure; and
   control circuitry configured to:
      detect whether the RF MR signal receiving coil is coupled to the connector on the bed top plate, and
      control a movement of the bed top plate in an up-down direction to prevent the RF MR signal receiving coil and/or a cable of the RF MR signal receiving coil from being damaged, based on a result of the detection,
      wherein, when the stretcher apparatus is jointly coupled with the bed structure and the RF MR signal receiving coil is coupled with the connector,
   the control of the movement of the bed top plate in the up-down direction comprises:
      (a) preventing the bed top plate from being raised when an operation to raise the bed top plate is done while the RF MR receiving coil is detected as being coupled with the connector, and
      (b) raising the bed top plate when the operation to raise the bed top plate is redone after the RF MR signal receiving coil is detected as being decoupled.

2. The magnetic resonance imaging apparatus according to claim 1, wherein the control circuitry indicates an error when the operation to raise the bed top plate is done with the RF MR signal receiving coil coupled with the connector.

3. The magnetic resonance imaging apparatus according to claim 1, wherein, when the stretcher apparatus is jointly coupled with the bed and the RF MR signal receiving coil is not coupled with the connector, the control circuitry raises the bed top plate when an operation to raise the bed top plate is done.

4. The magnetic resonance imaging apparatus according to claim 3, wherein, the control circuitry automatically, after the bed top plate starts an ascent and before the bed top plate comes into contact with the stretcher top plate, pauses the ascent at a position below the stretcher top plate, and the control circuitry, after the pausing, again raises the bed top plate according to a redone operation to raise the bed top plate from the position so as to scoop up the stretcher top plate.

5. The magnetic resonance imaging apparatus according to claim 1, wherein,
when the stretcher apparatus is jointly coupled with the bed structure and the RF MR signal receiving coil is coupled with the connector, the control circuitry prevents the bed top plate from descending when an operation to lower the bed top plate is done-while the RF MR signal receiving coil is detected as being coupled with the connector, and
lowers the bed top plate when the operation to lower the bed top plate is redone after the RF MR signal receiving coil is detected as being decoupled.

6. The magnetic resonance imaging apparatus according to claim 5, wherein the control circuitry indicates an error when the operation to lower the bed top plate is done with the RF MR signal receiving coil coupled with the connector.

7. The magnetic resonance imaging apparatus according to claim 1, wherein, when the stretcher apparatus is jointly coupled with the bed structure and the RF MR signal receiving coil is not coupled with the connector, the control circuitry lowers the bed top plate when an operation to lower the bed top plate is done, and stops the bed top plate at a position where the joint coupling between the stretcher apparatus and the bed structure can be released.

8. The magnetic resonance imaging apparatus according to claim 1, wherein, when the stretcher apparatus is not jointly coupled with the bed structure and the RF MR signal receiving coil is coupled with the connector, the control circuitry raises the bed top plate to a position where the bed top plate can be horizontally shifted without a pause on the way when an operation to raise the bed top plate is done.

9. The magnetic resonance imaging apparatus according to claim 1, wherein, when the stretcher apparatus is not jointly coupled with the bed structure and the RF MR signal receiving coil is coupled with the connector, the control circuitry lowers the bed top plate to a limit position of the bed top plate without a pause on the way when an operation to lower the bed top plate is done.

10. The magnetic resonance imaging apparatus according to claim 1, wherein the control circuitry controls a horizontal shift of the bed top plate correspondingly to where the connector is coupled to the RF MR signal receiving coil.

11. A magnetic resonance imaging (MRI) apparatus comprising:
a radio frequency (RF) MR signal receiving coil;
a gantry provided with a connector thereon, the connector being configured to be coupled with the RF MR signal receiving coil;
a bed top plate;
a bed structure which supports the bed top plate, the bed structure being configured to shift the bed top plate vertically and horizontally so as to position the object to be imaged within the gantry, the bed structure being configured to be jointly coupled with a stretcher apparatus having a stretcher top plate, and the stretcher top plate being placed on top of the bed top plate when the stretcher apparatus is jointly coupled with the bed structure; and
control circuitry configured to:
detect whether the RF MR signal receiving coil is coupled to the connector on the gantry, and
control a movement of the bed top plate in an up-down direction to prevent the RF MR signal receiving coil and/or a cable of the RF MR signal receiving coil from being damaged, based on a result of the detection,
wherein, when the stretcher apparatus is jointly coupled with the bed structure and the RF MR signal receiving coil is coupled with the connector,
the control of the movement of the bed top plate in the up-down direction comprises:
(a) preventing the bed top plate from being raised when an operation to raise the bed top plate is done while the RF MR signal receiving coil is detected as being coupled with the connector, and
(b) raising the bed top plate when the operation to raise the bed top plate is redone after the RF MR signal receiving coil is detected as being decoupled.

12. A method for controlling a magnetic resonance imaging (MRI) apparatus having a radio frequency (RF) MR signal receiving coil, a bed top plate configured to support an object to be imaged, said bed plate being provided with a connector thereon, the connector being configured to be coupled with the RF MR signal receiving coil, the magnetic resonance imaging apparatus having a bed structure which supports the bed top plate, the bed structure being configured to shift the bed top plate vertically and horizontally so as to position the object to be imaged within an imaging volume of an MRI system, the bed structure being configured to be jointly coupled with a stretcher apparatus having a stretcher top plate, the magnetic resonance imaging apparatus having control circuitry configured to control a vertical shift and a horizontal shift of the bed top plate, the stretcher top plate being configured to be placed on top of the bed top plate when the stretcher apparatus is jointly coupled with the bed structure, the method comprising:
using the control circuitry, detecting whether the RF MR signal receiving coil is coupled to the connector on the bed plate; and controlling a movement of the bed top plate in an up-down direction to prevent the RF MR signal receiving coil and/or a cable of the RF MR signal receiving coil from being damaged, based on a result of the detection,
wherein, when the stretcher apparatus is jointly coupled with the bed structure and the RF MR receiving coil is coupled with the connector,
the controlling of the movement of the bed top plate in the up-down direction comprises:
(a) preventing the bed top plate from being raised when an operation to raise the bed top plate is done while the RF MR receiving coil is detected as being coupled with the connector, and
(b) raising the bed top plate when the operation to raise the bed top plate is redone after the RF MR receiving coil is detected as being decoupled.

13. The method for controlling the magnetic resonance imaging apparatus according to claim 12, wherein when the stretcher apparatus is jointly coupled with the bed structure and the RF MR signal receiving coil is not coupled with the connector, the control circuitry raises the bed top plate when an operation to raise the bed top plate is done.

14. The method for controlling the magnetic resonance imaging apparatus according to claim 13, wherein the control circuitry automatically, after the bed top plate starts an ascent and before the bed top plate comes into contact with the stretcher top plate, pauses the ascent at a position below the stretcher top plate, and the control circuitry, after the pausing, again raises the bed top plate according to a redone operation to raise the bed top plate so as to scoop up the stretcher top plate.

15. The method for controlling the magnetic resonance imaging apparatus according to claim 12, wherein
when the stretcher apparatus is jointly coupled with the bed structure and the RF MR signal receiving coil is coupled with the connector, the control circuitry prevents the bed top plate from descending when an operation to lower the bed top plate is done-while the RF MR signal receiving coil is detected as being coupled with the connector, and
lowers the bed top plate when the operation to lower the bed top plate is redone after the RF MR signal receiving coil is detected as being decoupled.

16. The method for controlling the magnetic resonance imaging apparatus according to claim 12, wherein when the stretcher apparatus is jointly coupled with the bed structure and the RF MR signal receiving coil is not coupled with the connector, the control circuitry lowers the bed top plate when an operation to lower the bed top plate is done, and stops the bed top plate at a position where the joint coupling between the stretcher apparatus and the bed structure can be released.

17. The method for controlling the magnetic resonance imaging apparatus according to claim 12, wherein when the stretcher apparatus is not jointly coupled with the bed structure and the RF MR signal receiving coil is coupled with the connector, the control circuitry raises the bed top plate to a position where the bed top plate can be horizontally shifted without a pause on the way when an operation to raise the bed top plate is done.

* * * * *